United States Patent [19]
Andersen et al.

[11] Patent Number: 6,100,253
[45] Date of Patent: Aug. 8, 2000

[54] TRICYCLE SUBSTITUTED WITH AZAHETEROCYCLIC CARBOXYLIC ACIDS

[75] Inventors: Knud Erik Andersen, Smorum; Tine Krogh Jørgensen, Ølstykke; Rolf Hohlweg, Kvistgaard; Erik Fischer, Copenhagen S; Uffe Bang Olsen, Vallensbæk, all of Denmark; Zdenek Polivka, Prague, Czech Rep.; Karel Sindelar, Prague, Czech Rep.; Vladimir Valenta, Prague, Czech Rep.

[73] Assignee: Novo Nordisk A/S, Baesvaerd, Denmark

[21] Appl. No.: 09/376,734

[22] Filed: Aug. 17, 1999

Related U.S. Application Data

[62] Division of application No. 09/098,579, Jun. 17, 1998.
[60] Provisional application No. 60/051,833, Jul. 7, 1997.

[30] Foreign Application Priority Data

Jun. 25, 1997 [DK] Denmark ................... 0751/97

[51] Int. Cl.[7] .................. A61K 31/55; A61K 31/445; C07J 21/00; C07D 211/06; C07D 307/48
[52] U.S. Cl. .................. 514/211.1; 514/329; 514/408; 514/431; 514/437; 540/10; 540/12; 540/26; 540/27; 546/203; 546/204; 549/488; 549/495
[58] Field of Search ................ 546/203, 204; 514/329, 408, 211.1, 431, 437; 540/10, 12, 26, 27; 549/488, 495

[56] References Cited

U.S. PATENT DOCUMENTS 5,595,989  1/1997  Andersen et al. ............. 514/217

FOREIGN PATENT DOCUMENTS

WO 95/18793  7/1995  WIPO .

*Primary Examiner*—Mukund J. Shah
*Assistant Examiner*—Tamthom N. Truong
*Attorney, Agent, or Firm*—Steve T. Zelson; Carol E. Rozek

[57] ABSTRACT

The present invention relates to novel N-substituted azaheterocyclic compounds of the general formula

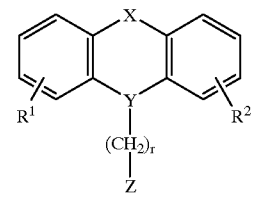

wherein X, Y, Z, $R^1$, $R^2$ and r are as defined in the detailed part of the present description, or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation as well as their use for treatment of indications caused by or related to the secretion and circulation of insulin antagonising peptides, e.g. non-insulin-dependent diabetes mellitus (NIDDM) and ageing-associated obesity.

15 Claims, No Drawings

TRICYCLE SUBSTITUTED WITH AZAHETEROCYCLIC CARBOXYLIC ACIDS

CROSS-REFERENCE TO RELATED APPLICATIONS

This application is a divisional of application Ser. No. 09/098,579 filed Jun. 17, 1998 and claims priority under 35 U.S.C. 119 of Danish application no. 0751/97 filed Jun. 25, 1997 and U.S. provisional application No. 60/051,833 filed Jul. 7, 1997, the contents of which are fully incorporated herein by reference.

FIELD OF INVENTION

The present invention relates to novel N-substituted azaheterocyclic compounds in which a substituted alkyl chain forms part of the N-substituent or salts thereof, to methods for their preparation, to compositions containing them, to the use of the compounds for preparing compositions for the clinical treatment of painful, hyperalgesic and/or inflammatory conditions in which C-fibres play a pathophysiological role by eliciting neurogenic pain or inflammation, and to methods of treating said painful, hyperalgesic and/or inflammatory conditions. The invention also relates to the use of the present compounds for the treatment of insulin resistance in non-insulin-dependent diabetes mellitus (NIDDM) as well as ageing-associated obesity, the present compounds being known to interfere with neuropeptide containing C-fibres and hence to inhibit the secretion and circulation of insulin antagonising peptides like CGRP or amylin.

BACKGROUND OF INVENTION

The nervous system exerts a profound effect on the inflammatory response. Antidromic stimulation of sensory nerves results in localised vasodilation and increased vascular permeability (Janecso et al. Br. J. Pharmacol. 1967, 31, 138–151), and a similar response is observed following injection of peptides known to be present in sensory nerves. From this and other data it is postulated that peptides released from sensory nerve endings mediate many inflammatory responses in tissues like skin, joint, urinary tract, eye, meninges, gastro-intestinal and respiratory tracts. Hence inhibition of sensory nerve peptide release and/or activity may be useful in treatment of for example arthritis, dermatitis, rhinitis, asthma, cystitis, gingivitis, thrombophlelitis, glaucoma, gastrointestinal diseases or migraine.

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or ageing-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or ageing.

In U.S. Pat. Nos. 4,383,999 and 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake.

WO 9518793, WO 9631498, WO 9631499 and WO 9631470 discloses N-substituted azaheterocyclic carboxylic acids and esters thereof. Unlike the compounds of said WO publications, the compounds of the present invention have an extended carboxyalkyl chain.

SUMMARY OF THE INVENTION

The present invention relates to compounds of the general formula 1, wherein X, Y, Z, $R^1$, $R^2$ and r are as defined in the detailed part of the present description.

The present compounds are useful for the treatment, prevention, elimination, alleviation or amelioration of an indication related to all painful, hyperalgesic and/or inflammatory conditions in which C-fibres play a pathophysiological role, e.g. neurogenic pain, neurogenic inflammation, migraine, neuropathy, itching and rheumatoid arthritis, as well as indications caused by or related to the secretion and circulation of insulin antagonising peptides and other peptides derived from the sensory nervous system, e.g. non-insulin-dependent diabetes mellitus (NIDDM) and ageing-associated obesity.

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

In another aspect of the present invention there is provided a method of treating painful, hyperalgesic and/or inflammatory conditions in which C-fibres play a pathophysiological role, e.g. neurogenic pain, neurogenic inflammation, migraine, neuropathy, itching and rheumatoid arthritis, as well as a method of treating indications caused by or related to the secretion and circulation of insulin antagonising peptides, e.g. non-insulin-dependent diabetes mellitus (NIDDM) and ageing-associated obesity.

The method of treatment may be described as the treatment, prevention, elimination, alleviation or amelioration of one of the above indications, which comprises the step of administering to the said subject a neurologically effective amount of a compound of the invention, or a pharmaceutically acceptable salt thereof.

A further aspect of the invention relates to the use of a compound of the present invention for the preparation of a pharmaceutical composition for the treatment of all painful, hyperalgesic and/or inflammatory conditions in which C-fibres play a pathophysiological role, e.g. neurogenic pain, neurogenic inflammation, migraine, neuropathy, itching and rheumatoid arthritis, as well as for the treatment of indications caused by or related to the secretion and circulation of insulin antagonising peptides and other peptides derived from the sensory nervous system, e.g. non-insulin-dependent diabetes mellitus (NIDDM) and ageing-associated obesity.

Further objects will become apparent from the following description.

DETAILED DESCRIPTION OF THE INVENTION

Accordingly, the present invention relates to novel N-substituted azaheterocyclic compounds of the general formula I

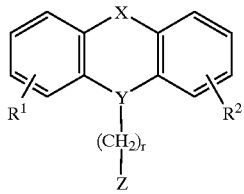

(I)

wherein $R^1$ and $R^2$ independently are hydrogen, halogen, trifluoromethyl, hydroxy, $C_{1-6}$-alkyl or $C_{1-6}$-alkoxy;

Y is >N—CH$_2$—, >CH—CH$_2$— or >C=CH— wherein only the underscored atom participates in the ring system;

X is ortho-phenylene, —O—, —S—, —C($R^6R^7$)—, —CH$_2$CH$_2$—, —CH=CH—CH$_2$—, —CH$_2$—CH=CH—, —CH$_2$—(C=O)—, —(C=O)—CH$_2$—, —CH$_2$CH$_2$CH$_2$—, —CH=CH—, —N($R^8$)—(C=O)—, —(C=O)—N($R^8$)—, —O—CH$_2$—, —CH$_2$—O—, —OCH$_2$O—, —S—CH$_2$—, —CH$_2$—S—, —(CH$_2$)N($R^8$)—, —N($R^8$)(CH$_2$)—, —N(CH$_3$)SO$_2$—, —SO$_2$N(CH$_3$)—, —CH($R^{10}$)CH$_2$—, —CH$_2$CH($R^{10}$)—, —(C=O)—, —N($R^9$)— or —(S=O)— wherein $R^6$, $R^7$, $R^8$ and $R^9$ independently are hydrogen or $C_{1-6}$-alkyl; and wherein $R^{10}$ is $C_{1-6}$-alkyl or phenyl;

r is 1, 2 or 3; and

Z is selected from

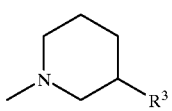

(a)

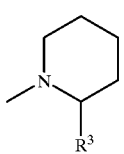

(b)

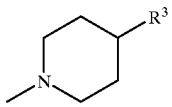

(c)

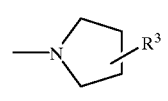

(d)

wherein $R^3$ is —(CH$_2$)$_p$COOH wherein p is 2, 3, 4, 5 or 6; or a pharmaceutically acceptable salt thereof.

The compounds of formula I may exist as geometric and optical isomers and all isomers, as separated, pure or partially purified stereoisomers or racemic mixtures thereof are included in the scope of the invention. Isomers may be separated by means of standard methods such as chromatographic techniques or fractional crystallisation of suitable salts.

Preferably, the compounds of formula I exist as the individual geometric or optical isomers.

The compounds according to the invention may optionally exist as pharmaceutically acceptable acid addition salts, metal salts or, optionally alkylated, ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts. Further examples of pharmaceutically acceptable inorganic or organic acid addition salts include the pharmaceutically acceptable salts listed in *Journal of Pharmaceutical Science*, 66, 2 (1977) which are known to the skilled artisan.

Also intended as pharmaceutically acceptable acid addition salts are the hydrates which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of formula I may be administered in a pharmaceutically acceptable acid addition salt form or where possible as a metal or a lower alkylammonium salt. Such salt forms exhibit approximately the same order of activity as the free base forms.

In the above structural formula and throughout the present specification, the following terms have the indicated meaning:

The term "$C_{1-6}$-alkyl" as used herein, alone or in combination, refers to a straight or branched, saturated hydrocarbon chain having 1 to 6 carbon atoms. Typical $C_{1-6}$-alkyl groups include, but are not limited to, methyl, ethyl, n-propyl, iso-propyl, n-butyl, sec-butyl, iso-butyl, tert-butyl, n-pentyl, iso-pentyl, 2-methylbutyl, 3-methylbutyl, n-hexyl, iso-hexyl, 4-methylpentyl, neopentyl, 1,2-dimethylpropyl, 2,2-dimethylpropyl, 1,2,2-trimethylpropyl and the like.

The term "$C_{1-6}$-alkoxy" as used herein, alone or in combination is intended to include those $C_{1-6}$-alkyl groups of the designated length in either a linear or branched or cyclic configuration linked through an ether oxygen having its free valence bond from the ether oxygen. Examples of linear alkoxy groups are methoxy, ethoxy, propoxy, butoxy, pentoxy and hexoxy. Examples of branched alkoxy are isopropoxy, sec-butoxy, tert-butoxy, isopentoxy and isohexoxy. Example of cyclic alkoxy are cyclopropyloxy, cyclobutyloxy, cyclopentyloxy and cyclohexyloxy.

The term "halogen" means fluorine, chlorine, bromine or iodine.

In a preferred embodiment of the invention $R^1$ and $R^2$ are selected from hydrogen, halogen, trifluoromethyl or $C_{1-6}$-alkyl. Preferably $R^1$ and $R^2$ are hydrogen or halogen.

In another preferred embodiment of the invention X is selected from —O—, —S—, —CH$_2$CH$_2$—, —CH=CH—, —O—CH$_2$—, —CH$_2$—O—, —OCH$_2$O—, —S—CH$_2$— or —CH$_2$—S—. Preferably X is —CH$_2$CH$_2$—.

In another preferred embodiment of the invention Y is >C=CH— or >N—CH$_2$—. Preferably Y is >C=CH—.

In another preferred embodiment of the invention Z is selected from

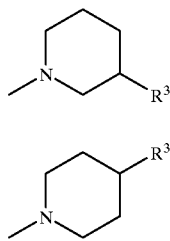

wherein $R^3$ is —$(CH_2)_p$COOH and p is 2, 3, 4, 5 or 6;

In yet another preferred embodiment of the invention p is 2 or 3.

Preferred compounds of the present invention include:

3-(1-(3-(10,11-Dihydrodibenzo[a,d]cyclohepten-5-ylidene)-1-propyl)piperidin-3-yl)propionic acid, 3-(1-(3-(10,11-Dihydrodibenzo[b,f]azepin-5-yl)-1-propyl)piperidin-3-yl)propionic acid, 3-(1-(2-(10,11-Dihydrodibenzo[a,d]cyclohepten-5-ylidene)ethyl)piperidin-4-yl)propionic acid, 3-(1-(3-(10,11-Dihydro-5H-dibenzo[a,d]cyclohepten-5-ylidene)-1-propyl)piperidin-4-yl)propionic acid, 3-(1-(3-(10,11-Dihydro-5H-dibenzo[b,f]azepin-5-yl)-1-propyl)piperidin-4-yl)propionic acid, 3-(1-(3-(Thioxanthen-9-ylidene)-1-propyl)piperidin-4-yl)propionic acid, 3-(1-(3-(Xanthen-9-ylidene)-1-propyl)piperidin-4-yl)propionic acid, 3-(1-(3-(12H-Dibenzo[d,g][1,3]dioxocin-12-ylidene)-1-propyl)piperidin-4-yl)propionic acid, 4-(1-(3-(10,11-Dihydro-5H-dibenzo[a,d]cyclohepten-5-ylidene)-1-propyl)piperidin-4-yl)-butyric acid, 3-(1-(3-(10,11-Dihydro-5H-dibenzo[a,d]cyclohepten-5-ylidene)-1-propyl)piperidin-2-yl)propionic acid, 3-(1-(3-(1-Bromo-10,11-dihydro-5H-dibenzo[a,d]cyclohepten-5-ylidene)-1-propyl)piperidin-4-yl)propionic acid, or a pharmaceutically acceptable salt thereof.

Other preferred compounds of the invention include:

3-(1-(3-(2-Fluoro-10,11-dihydro-5H-dibenzo[a,d]cyclohepten-5-ylidene)-1-propyl)piperidin-4-yl)propionic acid;

3-(1-(3-(2-Trifluoromethyl-10,11-dihydro-5H-dibenzo[a,d]cyclohepten-5-ylidene)-1-propyl)piperidin-4-yl)propionic acid;

3-(1-(3-(2-Hydroxy-10,11-dihydro-5H-dibenzo[a,d]cyclohepten-5-ylidene)-1-propyl)piperidin-4-yl)propionic acid;

3-(1-(3-(2-Methyl-10,11-dihydro-5H-dibenzo[a,d]cyclohepten-5-ylidene)-1-propyl)piperidin-4-yl)propionic acid;

3-(1-(3-(2-Methoxy-10,11-dihydro-5H-dibenzo[a,d]cyclohepten-5-ylidene)-1-propyl)-piperidin-4-yl)propionic acid;

3-(1-(3-(10,11-Dihydro-5H-dibenzo[a,d]cyclohepten-5-yl)-1-propyl)piperidin-4-yl)propionic acid;

3-(1-(3-(6,11-Dihydro-dibenz[b,e]thiepin-11-ylidene)-1-propyl)piperidin-4-yl)propionic acid;

3-(1-(3-(2-Fluoro-6,11-dihydro-dibenz[b,e]thiepin-11-ylidene)-1-propyl)piperidin-4-yl)propionic acid;

4-(1-(3-(6,11-Dihydro-dibenz[b,e]thiepin-11-ylidene)-1-propyl)piperidin-4-yl)butyric acid;

3-(1-(3-(6,11-Dihydro-dibenz[b,e]thiepin-11-ylidene)-1-propyl)piperidin-3-yl)propionic acid;

3-(1-(3-(6,11-Dihydro-dibenz[b,e]thiepin-11-ylidene)-1-propyl)piperidin-2-yl)propionic acid;

3-(1-(3-(10,11-Dihydro-5H-dibenzo[a,d]cyclohepten-5-ylidene)-1-propyl)pyrrolidin-3-yl)propionic acid;

4-(1-(3-(10,11-Dihydro-5H-dibenzo[a,d]cyclohepten-5-ylidene)-1-propyl)pyrrolidin-3-yl)butyric acid;

3-(1-(3-(6,11-Dihydro-dibenz[b,e]thiepin-11-ylidene)-1-propyl)pyrrolidin-3-yl)propionic acid;

3-(1-(3-(10H-Anthracen-9-ylidene)-1-propyl)pyrrolidin-3-yl)propionic acid;

3-(1-(3-(Dibenzo[a,d]cyclohepten-5-ylidene)-1-propyl)pyrrolidin-3-yl)propionic acid;

3-(1-(3-(10H-Anthracen-9-ylidene)-1-propyl)piperidin-4-yl)propionic acid;

3-(1-(3-(Dibenzo[a,d]cyclohepten-5-ylidene)-1-propyl)piperidin-4-yl)propionic acid;

5-(1-(3-(10,11-Dihydro-5H-dibenzo[a,d]cyclohepten-5-yl)-1-propyl)piperidin-4-yl)pentanoic acid;

5-(1-(3-(6,11-Dihydro-dibenz[b,e]thiepin-11-ylidene)-1-propyl)piperidin-4-yl)pentanoic acid;

5-(1-(3-(Thioxanthen-9-ylidene)-1-propyl)piperidin-4-yl)pentanoic acid;

5-(1-(3-(12H-Dibenzo[d,g][1,3]dioxocin-12-ylidene)-1-propyl)piperidin-4-yl)pentanoic acid or a pharmaceutically acceptable salt thereof.

It has been demonstrated that the novel compounds of formula I inhibit neurogenic inflammation which involves the release of neuropeptides from peripheral and central endings of sensory C-fibres. Experimentally this can be demonstrated in animal models of histamine induced paw oedema Amann et al. (Europ. J. Pharmacol. 279, 227–231, 1995) in which the novel compounds of formula I exhibit a potent inhibitory effect. Compounds of formula I may be used to treat all painful, hyperalgesic and/or inflammatory conditions in which C-fibres play a pathophysiological role by eliciting neurogenic pain or inflammation, i.e.:

Acutely painful conditions exemplified by migraine, post-operative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, itching, chronic pancreatitis, inflammatory skin disease including psoriasis and autoimmune dermatoses, osteoporotic pain.

Further, it has been demonstrated that the compounds of general formula I improves the glucose tolerance in diabetic ob/ob mice and that this may result from the reduced release of CGRP from peripheral nervous endings. Hence the compounds of general formula I may be used in the treatment of NIDDM as well as ageing-associated obesity. Experimentally this has been demonstrated by the subcutaneous administration of glucose into ob/ob mice with or without previous oral treatment with a compound of general formula I.

The compounds of formula I may be prepared by the following method:

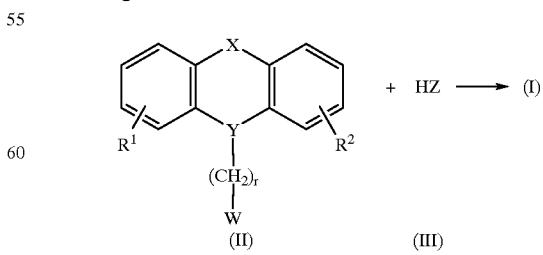

A compound of formula II wherein $R^1$, $R^2$, X, Y and r are as defined above and W is a suitable leaving group such as halogen, p-toluene sulphonate or mesylate may be reacted with an aza compound of formula III wherein Z is as defined above. This alkylation reaction may be carried out in a solvent such as acetone, dibutylether, 2-butanone, methyl ethyl ketone, ethyl acetate, tetrahydrofuran (THF) or toluene in the presence of a base e.g. sodium hydride or potassium carbonate and a catalyst, e.g. an alkali metal iodide at a temperature up to reflux temperature for the solvent used for e.g. 1 to 120 h.

Compounds of formula II and III may readily be prepared by methods familiar to those skilled in the art.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

PHARMACOLOGICAL METHODS

I. Histamine Induced Paw Oedema

The rat histamine paw oedema test was performed essentially as described by Amann et al. (Europ. J. Pharmacol. 279, 227–231, 1995). In brief 250–300 g male Sprague-Dawley rats were anaesthetized with pentobarbital sodium, and placed on a 32 degree heated table. Ten minutes later histamine (50 micoliter, 3 mg/ml) was injected in the right hind paw and 20 minutes hereafter the paw swelling was determined by water plethysmography (Ugo Basile). Test compounds were administered intraperitoneally at 15 minutes before the anaesthetics.

II. Histamine Induced Hyperglycemia in Mice

Conscious unfasted 25 g male NMRI mice are administered histamine chloride (90 nmol) icv according to the method of Nishibori et al. (J. Pharmacol. Exp. Therap. 241, 582–286, 1987). Blood glucose is determined at time 0 and 40 min after the histamine injection. Test compounds are administered at 1.0 mg/kg ip 30 min before the histamine injection, and % inhibition refers to the capacity of the compounds to inhibit the histamine induced blood glucose rise.

III. Reduced Release of CGRP ob/ob female mice, 16 weeks of age, where injected glucose (2 g/kg) subcutaneously. At times hereafter blood glucose was determined in tail venous blood by the glucose oxidase method. At the end of the study the animals were decapitated and trunck blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

Values for inhibition of histamine induced oedema response for a representative compound is listed in table I.

TABLE I

Inhibition of histamine induced paw oedema at 1.0 mg/kg

| Example no. | % inhibition |
|---|---|
| 1 | 22 |

Values for inhibition of histamine induced hyperglycemia for a representative compound is listed in table II.

TABLE II

Inhibition of histamine induced hyperglycemia at 1.0 mg/kg

| Example no. | % inhibition |
|---|---|
| 1 | 42 |

PHARMACEUTICAL COMPOSITIONS

The present invention also relates to pharmaceutical compositions comprising, as an active ingredient, at least one of the compounds of the general formula I or a pharmaceutically acceptable salt thereof and, usually, such compositions also contain a pharmaceutically acceptable carrier or diluent.

Pharmaceutical compositions comprising a compound of the present invention may be prepared by conventional techniques, e.g. as described in *Remington: The Science and Practise of Pharmacy*, 19$^{th}$ Ed., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, syrup, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, topical, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of an indication related to all painful, hyperalgesic and/or inflammatory conditions in which C-fibres play a pathophysiological role such as e.g. neurogenic pain, neurogenic inflammation, migraine, neuropathy, itching and rheumatoid arthritis, as well as indications caused by or related to the secretion and circulation of insulin antagonising peptides, such as non-insulin-dependent diabetes mellitus (NIDDM) or ageing-associated obesity. Such mammals include also animals, both domestic animals, e.g. household pets, and non-domestic animals such as wildlife.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, in an effective amount.

The compounds of the invention are effective over a wide dosage range. For example, in the treatment of humans, dosages from about 0.5 to about 1000 mg, preferably from about 1 to about 500 mg of compounds of formula I, conveniently given from 1 to 5 times daily. A most preferable dosage is from about 50 to about 200 mg per dose when administered to e.g. a human. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 50 to about 200 mg of active ingredient in or together with a pharmaceutically acceptable carrier per unit dosage.

Usually, dosage forms suitable for oral, nasal, pulmonal or transdermal administration comprise from about 0.5 mg to about 1000 mg, preferably from about 1 mg to about 500 mg of the compounds of formula I admixed with a pharmaceutically acceptable carrier or diluent.

The method of treating may be described as the treatment of an indication caused by or related to the secretion and circulation of insulin antagonising peptides like CGRP or amylin in a subject in need thereof, which comprises the step of administering to the said subject a neurologically effective amount of a compound of the invention, or a pharmaceutically acceptable salt thereof.

Any novel feature or combination of features described herein is considered essential to this invention.

EXAMPLES

The process for preparing compounds of formula I and preparations containing them is further illustrated in the following examples, which, however, are not to be construed as limiting.

Hereinafter, TLC is thin layer chromatography, $CDCl_3$ is deuterio chloroform and DMSO-$d_6$ is hexadeuterio dimethylsulfoxide. The structures of the compounds are confirmed by either elemental analysis or NMR, where peaks assigned to characteristic protons in the title compounds are presented where appropriate. $^1$H NMR shifts ($\delta_H$) are given in parts per million (ppm). M.p. is melting point and is given in ° C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1

3-(1-(3-(10,11-Dihydrodibenzo[a,d]cyclohepten-5-ylidene)-1-propyl)piperidin-3-yl)propionic acid hydrochloride

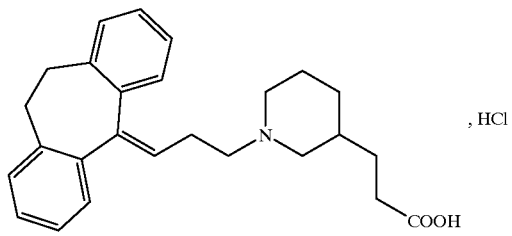

A mixture of 3-(3-pyridyl)acrylic acid (5.0 g, 33.5 mmol), 5% Rhodium on carbon (1 g) and 1 N hydrochloric acid (75 ml) was placed under an atmosphere of hydrogen at 8 atm. for 20 h. The reaction mixture was filtered and from the filtrate, the solvent was evaporated in vacuo. This afforded 3-(piperidin-3-yl)propionic acid hydrochloride (6.0 g, 92%) as a solid.

M.p. 233–234° C.

¹H-NMR (DMSO-d₆) δ1.0–1.2 (m, 1H), 1.35–1.80 (m, 6H), 2.25 (t, 2H), 2.48 (q, 1H), 2.70 (q, 1H), 3.15 (d, 2H), 8.9 (d, 1H), 9.2 (d, 1H), 12.1 (brs, 1H).

To a solution of 3-(piperidin-3-yl)propionic acid (3.0 g, 15.5 mmol) in ethanol (25 ml) was added 4 spoonful of MgSO₄ and 10 drops of concentrated sulfuric acid. The reaction mixture was heated at reflux temperature overnight and then filtered. The solvent was evaporated in vacuo and to the residue was added ethanol (25 ml), 4 spoonful of MgSO₄ and 10 drops of concentrated sulfuric acid. The reaction mixture was heated at reflux temperature overnight and then filtered. The solvent was evaporated in vacuo and to the residue cold saturated aqueous potassium carbonate (10 ml) was added. The mixture was extracted with dichloromethane (3×100 ml) and the combined organic extracts were dried (MgSO₄), filtered, and the solvent evaporated in vacuo. This afforded 3-(piperidin-3-yl)propionic acid ethyl ester (2.4 g, 84%).

¹H-NMR (DMSO-d6) δ0.9–1.0 (m, 1H), 1.15 (t, 3H), 1.25–1.45 (m, 4H), 1.45–1.60 (m, 1H), 1.72 (d, 1H), 2.10 (t, 1H), 2.28 (t, 2H), 2.39 (dt, 1H), 2.85 (t, 2H), 3.25 (brs, 1H), 4.05 (q, 2H).

To a solution of 5-(3-bromo-1-propylidene)-10,11-dihydro-5H-dibenzo[a,d]cycloheptene (1.77 g, 5.64 mmol) in N,N-dimethyl formamide (10 ml) was added the above ester (1.15 g, 6.2 mmol) and potassium carbonate (1.6 g, 11.3 mmol) and the mixture was stirred overnight.

The mixture was filtered and the filtercake was washed with toluene. The solvent was evaporated in vacuo and water (25 ml) was added to the residue. The resulting mixture was extracted with ethyl acetate (2×100 ml) and the combined organic extracts were washed with brine (5 ml), dried (MgSO₄) and filtered. The solvent was evaporated in vacuo to give an oily residue (2.7 g) which was purified by column chromatography on silica gel using ethyl acetate as eluent. This afforded 3-(1-(3-(10,11-dihydrodibenzo[a,d]cyclohepten-5-ylidene)-1-propyl)piperidin-3-yl)propionic acid ethyl ester (2.0 g, 85%) as an oil.

¹H-NMR (CDCl₃) δ0.754.90 (m, 1H), 1.25 (t, 3H), 1.4–1.8 (m, 8H), 2.25–2.45 (m, 6H), 2.7–2.85 (m, 3H), 2.9–3.05 (brs, 1H), 3.15–3.50 (brd, 2H), 4.10 (q, 2H), 5.84 (t, 1H), 7.0–7.3 (m, 8H).

The above ester (2.0 g, 4.8 mmol), dissolved in a mixture of ethanol (10 ml) and 4 N sodium hydroxide (2.4 ml) was stirred at ambient temperature for 1.5 h. A 4 N hydrochloric acid solution (3.6 ml) was added and the mixture was stirred for 3 minutes. Water (5 ml) and dichloromethane (100 ml) were added. The phases were separated and the organic phase was dried (MgSO₄), filtered and the solvent was removed in vacuo. The residue was re-evaporated with dichloromethane (10 ml), acetone (2×15 ml) and then stirred with acetone for 5–10 minutes. The solid was isolated by filtration and dried to give the title compound (2.0 g, 98%) as an amorphous solid.

¹H-NMR (DMSO-d₆) δ0.9–1.1 (m, 1H), 1.65–1.90 (m, 2H), 2.25 (dt, 2H), 2.4–2.9 (m, 8H), 3.1–3.4 (m, 8H), 5.80 (t, 1H), 7.05–7.30 (m, 8H), 10.15 (s, 1H), 12.1 (s, 1H).

Calculated for C₂₆H₃₁NO₂, HCl, H₂O

C, 70.33%; H, 7.72%; N, 3.15%; Found: C: 70.5%; H: 7.4%; N: 3.2%.

Example 2

3-(1-(3-(10,11-Dihydrodibenzo[b,f]azepin-5-yl)-1-propyl)piperidin-3-yl)propionic acid hydrochloride

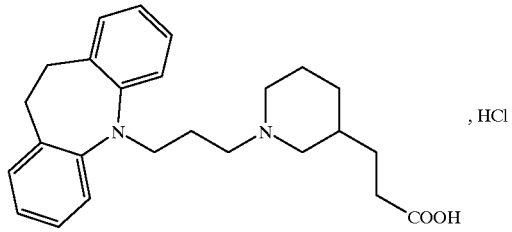

To a solution of 5-(3-chloro-1-propyl)-10,11-dihydrodibenzo[b,f]azepine (1.4 g, 5.2 mmol) in N,N-dimethyl formamide (10 ml) was added 3-(piperidin-3-yl) propionic acid ethyl ester (1.15 g, 6.2 mmol), potassium carbonate (2.14 g, 15.5 mmol) and potassium iodide (0.82 g, 4.9 mmol). The mixture was heated at 150° C. for 30 minutes when heating was discontinued and the mixture was stirred overnight. The mixture was filtered and the filtercake was washed with ethyl acetate. The solvent was evaporated in vacuo and water (25 ml) was added to the residue. The resulting mixture was extracted with ethyl acetate (2×100 ml) and the combined organic extracts were washed with brine (5 ml), dried (MgSO₄) and filtered. The solvent was evaporated in vacuo to give an oily residue (2.5 g) which was purified by column chromatography on silica gel using ethyl acetate as eluent. This afforded 3-(1-(3-(10,11-dihydrodibenzo[b,f]azepin-5-yl)propyl)piperidin-3-yl) propionic acid ethyl ester (1.5 g, 69%) as an oil.

¹H-NMR (CDCl₃) δ0.75–0.90 (m, 1H), 1.22 (t, 3H), 1.4–1.65 (m, 6H), 1.65–1.80 (m, 4H), 2.26 (dt, 2H), 2.35 (t, 2H), 2.72 (m, 2H), 3.13 (s, 4H), 3.75 (t, 2H), 4.10 (q, 2H), 6.90 (t, 2H), 7.05–7.15 (m, 6H).

The above ester (1.5 g, 3.6 mmol), dissolved in a mixture of ethanol (10 ml) and 4 N sodium hydroxide (1.8 ml) was stirred at ambient temperature for 2 h. A 4 N hydrochloric acid solution (2.7 ml) was added and the mixture was stirred for 3 minutes. Water (5 ml) and dichloromethane (100 ml) were added. The phases were separated and the organic phase was dried (MgSO₄), filtered and the solvent was removed in vacuo. The residue was re-evaporated with dichloromethane (10 ml), acetone (3×15 ml) and then stirred with isopropyl acetate. The gummy solid was isolated by filtration and dissolved in a mixture of dichloromethane (10 ml) and acetone (10 ml). The solvent was evaporated in vacuo and the residue was re-evaporated with acetone (3×15 ml). This afforded the title compound (1.25 g, 82%) as an amorphous solid.

¹H-NMR (DMSO-d₆) δ0.9–1.1 (m, 1H), 1.3–1.5 (m, 2H), 1.6–1.85 (m, 4H), 1.9 (m, 2H), 2.25 (t, 2H), 2.45 (m, 1H), 2.65 (m, 1H), 3.02 (t, 2H), 3.10 (s, 4H), 3.2–3.35 (m, 2H), 3.77 (t, 2H), 6.95 (m, 2H), 7.1 (m, 6H), 10.0 (brs, 1H), 12.1 (brs, 1H).

Calculated for C₂₅H₃₂N₂O₂, HCl, 3/2H₂O

C, 68.09%; H, 7.85%; N, 6.35%; Found: C: 67.8%; H: 7.7%; N: 6.2%.

Example 3
3-(1-(2-(10,11-Dihydrodibenzo[a,d]cyclohepten-5-ylidene)ethyl)piperidin-4-yl)propionic acid hydrochloride

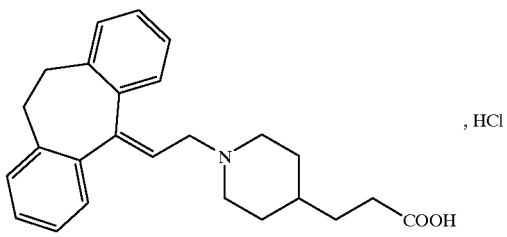

A mixture of 3-(4-pyridyl)acrylic acid (5.0 g, 33.5 mmol), 10% Palladium on carbon (0.5 g) and 1 N hydrochloric acid (80 ml) was placed under an atmosphere of hydrogen at 100 pSi. for 7 days. The reaction mixture was filtered and from the filtrate, the solvent was evaporated in vacuo. The residue was dissolved in 1 N hydrochloric acid (80 ml), 10% Palladium on carbon (0.5 g) was added and the mixture was placed under an atmosphere of hydrogen at 200 pSi. for 7 days. The reaction mixture was filtered and from the filtrate, the solvent was evaporated in vacuo to give a residue which was re-evaporated with dichloromethane (2×40 ml). This afforded 3-(piperidin-4-yl)propionic acid hydrochloride (6.2 g, 96%).

$^1$H-NMR (DMSO-d$_6$) δ1.30 (q, 2H), 1.45 (m, 3H), 1.75 (d, 2H), 2.25 (t, 2H), 2.75 (q, 2H), 3.20 (d, 2H), 8.85 (s,1H), 9.1 (s, 1H), 12.1 (brs, 1H).

To a mixture of 3(piperidin-4-yl)propionic acid (1.0 g, 5.2 mmol) in ethanol (25 ml) was added 3 spoonful of MgSO$_4$ and 6 drops of concentrated sulfuric acid. The reaction mixture was heated at reflux temperature overnight and then filtered. The solvent was evaporated in vacuo and to the residue was added cold saturated aqueous potassium carbonate (5 ml) was added. The mixture was extracted with cold dichloromethane (2×150 ml) and the combined organic extracts were dried (MgSO$_4$), filtered, and the solvent evaporated in vacuo. This afforded 3-(piperidin-4-yl) propionic acid ethyl ester in quantitative yield.

$^1$H-NMR (DMSO-d$_6$) δ1.0–1.2 (m, 5H), 1.35 (m, 1H), 1.45 (q, 2H), 1.60 (d, 2H), 2.28 (t, 2H), 2.55 (m, 2H), 3.00 (d, 2H), 4.05 (q, 2H).

To a solution of 5-(2-bromo-1-ethylidene)-10,11-dihydro-5H-dibenzo[a,d]cycloheptene (1.3 g, 4.3 mmol) in N,N-dimethyl formamide (10 ml) was added the above ester (0.96 g, 5.2 mmol) and potassium carbonate (1.4 g, 10.3 mmol) and the mixture was stirred overnight. Water (20 ml) was added and the resulting mixture was extracted with ethyl acetate (2×100 ml). The combined organic extracts were washed with brine (10 ml), dried (MgSO$_4$) and filtered. The solvent was evaporated in vacuo to give a residue (1.7 g) which was purified by column chromatography on silica gel using a mixture of ethyl acetate and heptane (2:1) as eluent. This afforded 3-(1-(2-(10,11-dihydrodibenzo[a,d]cyclohepten-5-ylidene)ethyl)piperidin-4-yl)propionic acid ethyl ester (1.4 g, 81%).

$^1$H-NMR (CDCl$_3$) δ1.1–1.3 (m, 6H), 1.5–1.8 (m, 5H), 1.95 (brs, 1H), 2.30 (t, 2H), 2.7–3.5 (m, 8H), 4.10 (q, 2H), 6.00 (t, 1H), 7.0–7.3 (m, 8H).

The above ester (1.4 g, 3.5 mmol), dissolved in a mixture of ethanol (10 ml) and 4 N sodium hydroxide (1.7 ml) was stirred at ambient temperature for 2.5 h. A 4 N hydrochloric acid solution (2.6 ml) was added and the mixture was stirred for 3 minutes. Water (5 ml) and dichloromethane (100 ml) were added. The phases were separated and the organic phase was dried (MgSO$_4$), filtered and the solvent was removed in vacuo. The residue was re-evaporated with dichloromethane (15 ml) and acetone (2×15 ml) to give title compound (1.2 g, 80%) as an amorphous solid.

$^1$H-NMR (DMSO-d$_6$) δ1.4–1.5 (s, 5H), 1.78 (d, 2H), 2.20 (t, 2H), 2.6–3.0 (m, 4H), 3.2–3.5 (m, 5H), 3.85 (brs, 1H), 6.15 (t, 1H), 7.10 (t, 2H), 7.15–7.33 (m, 6H), 10.8 (brs, 1H), 12.05 (brs, 1H).

Calculated for C$_{25}$H$_{29}$NO$_2$, HCl:
C, 72.89%; H, 7.34%; N, 3.40%; Found: C: 72.8%; H: 7.5%; N: 3.4%.

Example 4
3-(1-(3-(10,11-Dihydro-5H-dibenzo[a,d]cyclohepten-5-ylidene)-1-propyl)piperidin-4-yl)propionic acid hydrochloride

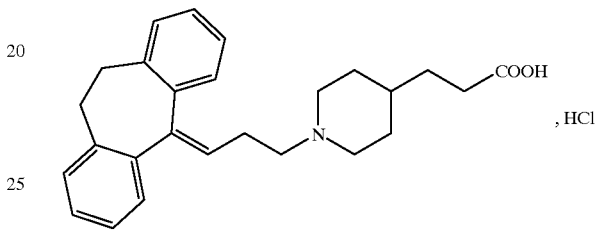

To a solution of 5-(3-bromo-1-propylidene)-10,11-dihydro-5H-dibenzo[a,d]cycloheptene (1.6 g, 5.2 mmol) in N,N-dimethyl formamide (10 ml) was added 3-(piperidinyl) propionic acid ethyl ester (0.96 g, 5.2 mmol) and potassium carbonate (1.4 g, 10.3 mmol) and the mixture was stirred for three days. The mixture was filtered and the filtercake was washed with ethyl acetate (100 ml). Water (50 ml) was added to the filtrate and the phases were separated. The aqueous phase was extracted with ethyl acetate (2×100 ml) and the combined organic extracts were dried (MgSO$_4$) and filtered. The solvent was evaporated in vacuo to give a residue (2 g) which was purified by column chromatography on silica gel using a mixture of ethyl acetate and heptane (1:1) as eluent. This afforded 3-(1-(3-(10,11-dihydrodibenzo[a,d]cyclohepten-5-ylidene)-1-propyl)piperidin-4-yl) propionic acid ethyl ester (1.5 g, 69%) as an oil.

$^1$H-NMR (CDCl$_3$) δ1.1–1.3 (m, 5H), 1.5–1.65 (m, 5H), 1.8 (brs, 2H), 2.38 (q, 4H), 2.4 (m, 2H), 2.80 (m, 3H), 2.95 (brs, 1H), 3.35 (brd, 2H), 4.10 (q, 2H), 5.83 (t, 1H), 7.0–7.3 (m, 8H).

The above ester (1.5 g, 3.6 mmol), dissolved in a mixture of ethanol (10 ml) and 4 N sodium hydroxide (1.8 ml) was stirred at ambient temperature for 2 h. A 4 N hydrochloric acid solution (2.7 ml) was added and the mixture was stirred for 2 minutes. Water (10 ml) and dichloromethane (100 ml) were added. The phases were separated and the organic phase was dried (MgSO$_4$), filtered and the solvent was removed in vacuo. The residue was re-evaporated with acetone (2×30 ml) and then stirred with acetone (10–20 ml) for 20 minutes. The solid was isolated by filtration and dried to give the title compound (1.5 g, 100%) as an amorphous solid.

$^1$H-NMR (DMSO-d$_6$) δ1.3–1.6 (s, 5H), 1.78 (d, 2H), 2.25 (t, 2H), 2.4–3.4 (m, 12H), 5.78 (t, 1H), 7.05–7.3 (m, 8H), 10.0 (brs, 1H), 12.05 (brs, 1H).

Calculated for C$_{26}$H$_{31}$NO$_2$, HCl:
C, 73.31%; H, 7.57%; N, 3.29%; Found: C: 73.02%; H: 7.83%; N: 3.03%.

Example 5

3-(1-(3-(10,11-Dihydro-5H-dibenzo[b,f]azepin-5-yl)-1-propyl)piperidin-4-yl)propionic acid hydrochloride

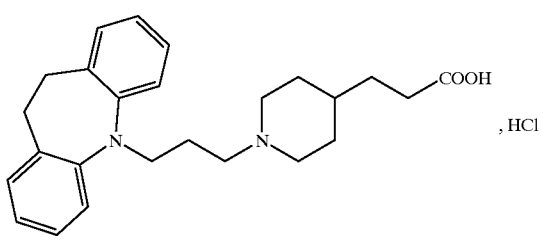

To a solution of 5-(3-chloro-1-propyl)-10,11-dihydrodibenzo[b,f]azepine (0.79 g, 2.9 mmol) in N,N-dimethyl formamide (10 ml) was added 3-(piperidin-4-yl) propionic acid ethyl ester (0.45 g, 2.4 mmol), potassium carbonate (0.67 g, 4.9 mmol) and potassium iodide (0.38 g, 2.3 mmol). The mixture was heated to 77° C. and then left at ambient temperature with stirring overnight. The mixture was then heated at 155° C. for 3 h and then allowed to cool. The mixture was poured into water (50 ml) and extracted with diethyl ether (3×150 ml). The combined organic extracts were dried (MgSO$_4$) and filtered. The solvent was evaporated in vacuo to give a residue (1.6 g) which was purified by column chromatography on silica gel using a mixture of ethyl acetate and heptane (1:1) as eluent. This afforded 3-(1-(3-(10,11-dihydrodibenzo[b,f]azepin-5-yl)-1-propyl)piperidin-4-yl)propionic acid ethyl ester (0.83 g, 78%).

$^1$H-NMR (CDCl$_3$) δ1.1–1.3 (m, 5H), 1.5–1.85 (m, 9H), 2.25–2.4 (m, 4H), 2.30 (d, 2H), 3.13 (s, 4H), 3.25 (t, 2H), 4.10 (q, 2H), 6.90 (t, 2H), 7.05–7.15 (m, 6H).

The above ester (0.8 g, 1.9 mmol), dissolved in a mixture of ethanol (10 ml) and 4 N sodium hydroxide (0.95 ml) was stirred at ambient temperature overnight. A 4 N hydrochloric acid solution (1.43 ml) was added and the mixture was stirred for 3 minutes. Water (10 ml) and dichloromethane (100 ml) were added. The phases were separated and the organic phase was dried (MgSO$_4$), filtered and the solvent was removed in vacuo. The residue was re-evaporated with acetone (2×30 ml) and then stirred with acetone (10–20 ml) for 20 minutes. The solid was isolated by filtration and dried to give the title compound (0.66 g, 81%) as an amorphous solid.

$^1$H-NMR (DMSO-d$_6$) δ1.3–1.6 (s, 5H), 1.75 (d, 2H), 1.90 (m, 2H), 2.22 (t, 2H), 2.75 (m, 2H), 3.00 (m, 2H), 3.10 (s, 4H), 3.3 (m, 2H), 3.75 (t, 2H), 6.95 (m, 2H), 7.05–7.15 (m, 6H), 9.8 (brs, 1H), 12.05 (brs, 1H).

Calculated for C$_{25}$H$_{29}$N$_2$O$_2$, HCl:

C, 69.99%; H, 7.75%; N, 6.53%; Found: C: 69.50%; H: 8.13%; N: 6.06%.

Example 6

3-(1-(3-(Thioxanthen-9-ylidene)-1-propyl)piperidin-4-yl) propionic acid acetate

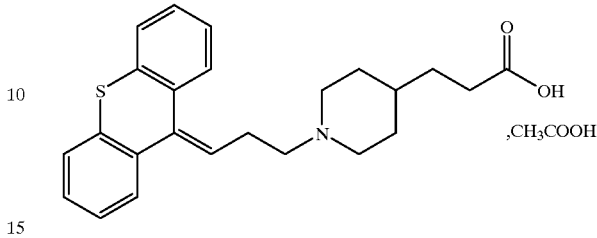

A mixture of 3-(thioxanthen-9-ylidene)-1-propylbromide (7.2 g, 0.0227 mol), ethyl 3-(piperidin-4-yl)propionate (6.3 g, 0.034 mol) and potassium carbonate (4.7 g, 0.034 mol) in N,N-dimethylformamide (40 ml) was stirred at room temperature for 100 h. The reaction mixture was diluted with water (250 ml), benzene (120 ml) was added and the mixture was stirred for 0.5 h. The phases were separated, and the benzene phase was washed with water (2×60 ml), brine (60 ml), dried (Na$_2$SO$_4$) and evaporated in vacuo. The residue (8.27 g) was purified by column chromatography on silica gel (160 g) using a mixture of light petroleum and ethyl acetate (1:2). This afforded 4.14 g (43%) of ethyl 3-(1-(3-(thioxanthen-9-ylidene)-1-propyl)piperidin-4-yl)propionate as an oil.

TLC: R$_f$=0.30 (SiO$_2$:n-hexane/ethyl acetate=1:1).

The free base was transformed into the corresponding hydrogen oxalate by treatment with oxalic acid dihydrate (1.24 g, 0.0098 mol) in dry acetone (50 ml) in a yield of 4.32 g (80%).

M.p. 168–170° C.

Calculated for C$_{26}$H$_{31}$NO$_2$S, C$_2$H$_2$O$_4$:

C, 65.73%; H, 6.50%; N, 2.74%; S, 6.27%. Found: C, 65.70%; H, 6.50%; N, 2.84%; S, 6.48%.

A mixture of ethyl 3-(1-(3-(thioxanthen-9-ylidene)-1-propyl)piperidin-4-yl)propionate (as the free base released from the above hydrogen oxalate; 3.71 g, 0.0088 mol), 4 N sodium hydroxide (10 ml) and 96% ethanol (70 ml) was stirred at room temperature overnight. Ethanol was evaporated in vacuo, the residue was dissolved in water (50 ml) and the aqueous solution was washed with diethyl ether (50 ml). The aqueous phase was neutralised with acetic acid and extracted with dichloromethane (3×150 ml). The combined dichloromethane extracts were dried (MgSO$_4$) and evaporated in vacuo. The residue was dissolved in acetone (30 ml), the solution was diluted with diethyl ether (30 ml) and the mixture was stirred for 1 h. The precipitated solid was filtered off, washed with acetone and dried in vacuo, affording 2.24 g (56%) of the title compound.

M.p. 190–220° C.

$^1$H NMR (250 MHz, DMSO-d$_6$) δ7.48–7.60 (m, 3H), 7.25–7.47 (m, 5H), 5.92 (t, 1H), 3.14 (d, 2H), 2.91 (t, 2H), 2.77 (t, 2H), 2.23 (t, 2H), 1.72 (d, 2H), 1.25–1.55 (m, 5H).

Calculated for C$_{24}$H$_{27}$NO$_2$S, C$_2$H$_4$O$_2$:

C, 68.85%; H, 6.89%; N, 3.09%; S, 7.07%; Found: C, 68.81%; H, 6.86%; N, 3.32%; S, 7.51%.

Example 7

3-(1-(3-(Xanthen-9-ylidene)-1-propyl)piperidin-4-yl)propionic acid hydrochloride

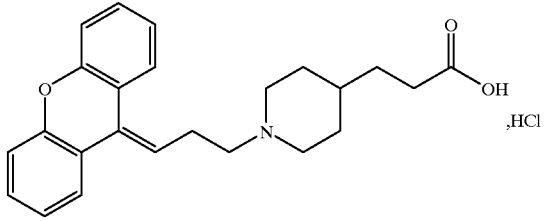

A mixture of 9-(3-bromopropylidene)xanthene (7.2 g, 24 mmol), ethyl 3-(piperidin-4-yl)propionate (4.4 g, 24 mmol), powdered dry potassium carbonate (8.3 g, 60 mmol) and N,N-dimethylformamide (46 ml) was stirred at 30° C. for 36 h. Benzene (200 ml) was added, and the benzene phase was washed with water (4×50 ml), dried ($Na_2SO_4$) and evaporated in vacuo. The residue (11.33 g) was purified by gradient column chromatography on silica gel (100 g) using benzene and ethyl acetate as eluents. This afforded 4.0 g (40%) of 3-(1-(3-(xanthen-9-ylidene)-1-propyl)piperidin-4-yl)propionic acid ethyl ester as an oil.

TLC: $R_f$=0.4 ($SiO_2$:chloroform).

A solution of the above base in acetone (20 ml) was treated with oxalic acid dihydrate (1.5 g, 11.8 mmol) in acetone (20 ml) to give 3.5 g (29%) of the corresponding hydrogen oxalate.

M.p. 186–188° C. (ethanol).

Calculated for $C_{26}H_{31}NO_3$, $C_2H_2O_4$, 0.25 $H_2O$:

C, 67.24%; H, 6.75%; N, 2.80%. Found: C, 67.46%; H, 7.00%; N, 2.73%.

The free base was released from the above hydrogen oxalate (3.14, 6.3 mmol) using 1 M sodium carbonate (20 ml), and extracted into ethyl acetate (30 ml). The solvent was evaporated in vacuo, affording the free base as an oil. This was then hydrolysed by addition of a mixture of 5 N sodium hydroxide (6 ml) and 96% ethanol (35 ml). The reaction mixture was stirred at 22° C. for 22 h and then at 33° C. for 1 h. The ethanol was evaporated in vacuo and the residue was dissolved in water (25 ml). The aqueous solution was washed with ether (2×20 ml), acidified with 2.5 N hydrochloric acid to pH 1 and extracted with dichloromethane (2×300 ml). The combined dichloromethane extracts were dried ($MgSO_4$) and evaporated in vacuo. Repeated evaporation from acetone provided a solid which was triturated with acetone (2×20 ml). The solid was filtered off, washed first with a mixture of ether and acetone (1:1) (3×10 ml) and then with ether (20 ml), affording 2.12 g (82%) of the title compound.

M.p. 218–221° C.

Calculated for $C_{24}H_{27}NO_3$, HCl, 0.25 $H_2O$:

C, 68.89%; H, 6.81%; N, 3.35%; Cl, 8.47%, Found: C, 69.15%; H, 6.80%; N, 3.25%; Cl, 8.34%.

Example 8

3-(1-(3-(12H-Dibenzo[d,g][1,3]dioxocin-12-ylidene)-1-propyl)piperidin-4-yl)propionic acid hydrochloride

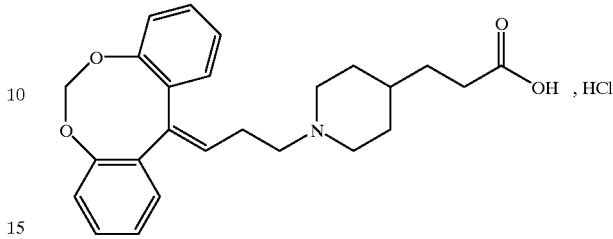

A mixture of 12-(3-bromo-1-propylidene)-12H-dibenzo[d,g][1,3]dioxocine (6.4 g, 0.0193 mol), ethyl 3-(piperidin-4-yl)propionate (3.93 g, 0.0213 mol), dried potassium carbonate (2.67 g, 0.0386 mol) and N,N-dimethylformamide (40 ml) was stirred at room temperature for 100 h. The reaction mixture was diluted with benzene (200 ml), the solution was washed with water (5×50 ml), dried ($MgSO_4$) and evaporated in vacuo. The crude oil (6.95 g) was purified by gradient column chromatography on silica gel (150 g) using benzene, benzene/chloroform and chloroform as eluents. The benzene and benzene/chloroform fractions were discarded, and the chloroform fractions afforded 4.67 g (56%) of 3-(1-(3-(12H-dibenzo[d,g][1,3]dioxocin-12-ylidine)-1-propyl)piperidin-4-yl)propionic acid ethyl ester as an oil.

TLC: $R_f$=0.28 ($SiO_2$:methanol/chloroform saturated with ammonia=1:100).

The above ester was dissolved in acetone (50 ml) and treated with a solution of oxalic acid dihydrate (1.42 g) in acetone (10 ml). The solution was diluted with diethyl ether (100 ml) and the precipitate was filtered off and re-crystallised from a mixture of ethanol (20 ml) and diethyl ether (40 ml). This afforded 3-(1-(3-(12H-dibenzo[d,g][1,3]-dioxocin-12-ylidene)-1-propyl)piperidin-4-yl)propionic acid ethyl ester hydrogen oxalate.

M.p. 153–155° C.

Calculated for $C_{27}H_{33}NO_4$, $C_2H_2O_4$:

C, 66.27%; H, 6.71%; N, 2.66%; Found: C, 66.13%; H, 6.72%; N, 2.57%.

To a solution of the above ester (free base liberated from hydrogen oxalate; 2.65 g, 0.0609 mol) in ethanol (15 ml), 15% sodium hydroxide (5 ml) was added and the mixture was stirred at room temperature for 2 h and left stirring overnight. The reaction mixture was diluted with dichloromethane (250 ml) and acidified with 4 N hydrochloric acid. The organic layer was separated, washed with water (10 ml), dried ($MgSO_4$) and evaporated. The residue was re-evaporated with acetone (2×30 ml), triturated with hot acetone (15 ml) and then added diethyl ether (5 ml). After cooling, the solid was filtered off, washed with ether and dried. This afforded 2.42 g (90%) of the title compound.

M.p. 226–230° C.

Calculated for $C_{25}H_{29}NO_4$, HCl, 0.25 $H_2O$:

C, 66.95%; H, 6.86%; N, 3.12%; Cl, 7.91%; Found: C, 66.73%; H, 6.77%; N, 3.18%; Cl, 8.20%.

Example 9

4-(1-(3-(10,11-Dihydro-5H-dibenzo[a,d]cyclohepten-5-ylidene)-1-propyl)piperidin-4-yl)-butyric acid hydrogen oxalate

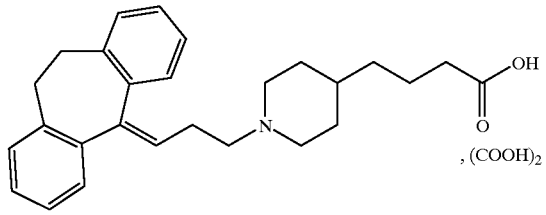

A mixture of 5-(3-bromopropylidene)-10,11-dihydro-5H-dibenzo[a,d]cycloheptene (5.8 g, 19.8 mmol), ethyl 4-(piperidin-4-yl)butyrate (6.1 g, 29 mmol), potassium carbonate (2.9 g, 21 mmol) and N,N-dimethylformamide (10 ml) was heated at 120° C. for 5 h. After cooling, benzene (50 ml) and water (50 ml) were added and the phases were separated. The organic phase was dried and the solvent was evaporated in vacuo. The residue was purified by column chromatography on silica gel (50 g) using mixtures of benzene and chloroform as eluents to give 6.9 g (83%) of 4-(1-(3-(10,11-dihydro-5H-dibenzo[a,d]cyclohepten-5-ylidene)-1-propyl)piperidin-4-yl)butyric acid ethyl ester as an oil.

TLC: $R_f$=0.56 (SiO$_2$:chloroform/ethanol/ammonium hydroxide=30:1:0.05).

The above ester (6.7 g, 15.9 mmol) was dissolved in ethanol (30 ml) and 20% sodium hydroxide (10 ml) was added. After stirring for 3 days, ethanol was evaporated in vacuo, water (50 ml) and diethyl ether (50 ml) were added and the phases were separated. The water phase was treated with acetic acid and extracted with dichloromethane. The organic phase was dried (MgSO$_4$) and the solvent was evaporated in vacuo. The residue (7.0 g) was dissolved in acetone (30 ml) and treated with a solution of oxalic acid dihydrate (2.0 g) in acetone (10 ml). The precipitate was filtered off and dried, affording 6.1 g (77%) of the title compound.

M.p. 122–128° C.

Calculated for $C_{27}H_{33}NO_2$, $C_2H_2O_4$, $H_2O$:

C, 68.08%; H, 7.29%; N, 2.74%; Found: C, 68.09%; H, 7.11%; N, 2.74%.

Example 10

3-(1-(3-(10,11-Dihydro-5H-dibenzo[a,d]cyclohepten-5-ylidene)-1-propyl)piperidin-2-yl)propionic acid

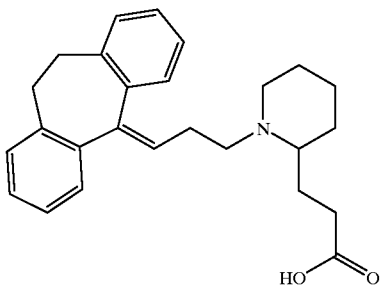

The title compound is prepared by the previously described method.

Example 11

3-(1-(3-(1-Bromo-10,11-dihydro-5H-dibenzo[a,d]cyclohepten-5-ylidene)-1-propyl)piperidin-4-yl)propionic acid

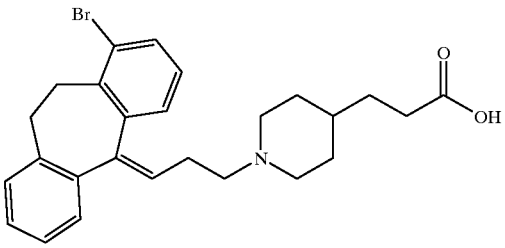

The title compound is prepared by the by the previously described method.

What is claimed is:

1. A compound of formula I

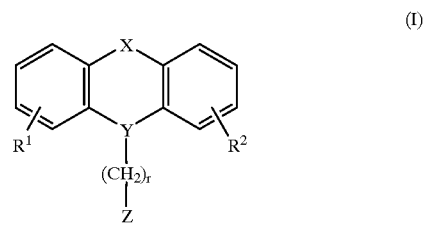

(I)

wherein $R^1$ and $R^2$ independently are hydrogen, halogen, trifluoromethyl, hydroxy, $C_{1-6}$-alkyl or $C_{1-6}$-alkoxy;

Y is >$\underline{C}$H—CH$_2$— or >$\underline{C}$=CH— wherein only the underscored atom participates in the ring system;

X is —S—, —S—CH$_2$—, —CH$_2$—S—, —N(CH$_3$)SO$_2$—, —SO$_2$N(CH$_3$)— or —S(=O)— r is 1, 2 or 3; and

Z is selected from

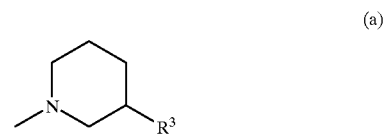
(a)

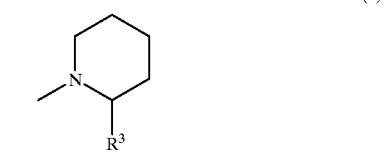
(b)

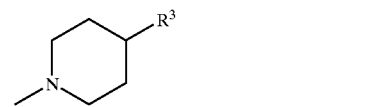
(c)

wherein $R^3$ is —(CH$_2$)$_p$COOH wherein p is 2, 3, 4, 5 or 6; or a pharmaceutically acceptable salt thereof.

2. A compound of claim 1 wherein $R^1$ and $R^2$ independently are hydrogen, halogen, trifluoromethyl or $C_{1-6}$-alkyl.

3. A compound of claim 1 wherein X is —S—.

4. A compound of claim 1 wherein Z is selected from (a)

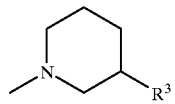

(c)

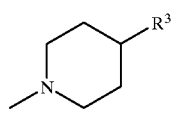

wherein $R^3$ is —$(CH_2)_p$COOH and p is 2, 3, 4, 5 or 6.

5. A compound of claim 1 wherein p is 2 or 3.

6. A compound of claim 1 which is 3-(1-(3-(Thioxanthen-9-ylidene)-1-propyl)piperidin-4-yl)propionic acid, or a pharmaceutically acceptable salt thereof.

7. A method of preparing a compound of claim 1, comprising: reacting a compound of formula II (II)

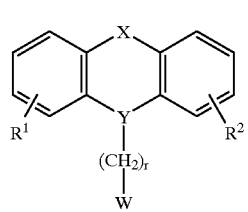

wherein $R^1$, $R^2$, X, Y and r are as defined in claim 1 and W is a suitable leaving group, with a compound of formula III

HZ         (III)

wherein Z is as defined in claim 1, to form a compound of formula I.

8. A pharmaceutical composition comprising as an active component an effective amount of a compound of claim 1 together with a pharmaceutically acceptable carrier or diluent.

9. The pharmaceutical composition of claim 8 comprising between 0.5 mg and 1000 mg of the compound.

10. A method of treating neurogenic inflammation comprising administering to a subject in need thereof an effective amount of a compound of claim 1.

11. A method of treating neurogenic inflammation comprising administering to a subject in need thereof a pharmaceutical composition according to claim 8.

12. A method of treating neurogenic inflammation associated with neuropathy or rheumatoid arthritis comprising administering to a subject in need thereof an effective amount of a compound of claim 1.

13. A method of treating neurogenic inflammation associated with neuropathy or rheumatoid arthritis comprising administering to a subject in need thereof a pharmaceutical composition of claim 8.

14. A method of treating insulin resistance in non-insulin-dependent diabetes mellitus (NIDDM) or ageing-associated obesity comprising administering to a subject in need thereof an effective amount of a compound of claim 1.

15. A method of treating insulin resistance in non-insulin-dependent diabetes mellitus (NIDDM) or ageing-associated obesity comprising administering to a subject in need thereof a pharmaceutical composition of claim 8.

\* \* \* \* \*

UNITED STATES PATENT AND TRADEMARK OFFICE
CERTIFICATE OF CORRECTION

PATENT NO. : 6,100,253
DATED : August 8, 2000
INVENTOR(S) : Andersen et al.

It is certified that error appears in the above-identified patent and that said Letters Patent is hereby corrected as shown below:

Column 11,
Line 21, please delete "(DMSO-d6)", and insert -- (DMSO-$d_6$) --.
Line 44, please delete "80.754.90", and insert -- 80.75-0.90 --.

Column 13,
Line 31, please delete "3(piperidin-4-yl)", and insert -- 3-(piperidin-4-yl) --.

Column 14,
Line 31, please delete "3-(piperidinyl)", and insert -- 3-(piperidin-4-yl) --.

Signed and Sealed this

Sixteenth Day of October, 2001

Attest:

NICHOLAS P. GODICI
Attesting Officer
Acting Director of the United States Patent and Trademark Office